(12) United States Patent
Achleitner et al.

(10) Patent No.: US 11,517,271 B2
(45) Date of Patent: Dec. 6, 2022

(54) COMPUTED TOMOGRAPHY DEVICE WITH A RADIATION PROTECTION APPARATUS FOR COVERING THE TUNNEL-SHAPED OPENING

(71) Applicant: Siemens Healthcare GmbH, Erlangen (DE)

(72) Inventors: Roman Achleitner, Nuremberg (DE); Stefan Lautenschlaeger, Nuremberg (DE); Hans-Juergen Mueller, Pretzfeld (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 0 days.

(21) Appl. No.: 17/325,549

(22) Filed: May 20, 2021

(65) Prior Publication Data
US 2021/0369214 A1  Dec. 2, 2021

(30) Foreign Application Priority Data
May 29, 2020 (DE) ..................... 10 2020 206 784.8

(51) Int. Cl.
*A61B 6/03* (2006.01)
*A61B 6/10* (2006.01)
*A61B 6/00* (2006.01)

(52) U.S. Cl.
CPC .............. *A61B 6/032* (2013.01); *A61B 6/107* (2013.01); *A61B 6/4452* (2013.01)

(58) Field of Classification Search
CPC ....... A61B 6/032; A61B 6/107; A61B 6/4452; A61B 6/4441; A61B 6/4405; A61B 6/035; A61B 6/44; A61B 6/4429; G21F 3/00
See application file for complete search history.

(56) References Cited

U.S. PATENT DOCUMENTS

| | | | |
|---|---|---|---|
| 4,977,585 A * | 12/1990 | Boyd | ..................... A61B 6/035 378/19 |
| 7,591,590 B2 | 9/2009 | Cadwalader et al. | |
| 8,057,097 B1 * | 11/2011 | Tybinkowski | ....... A61B 6/4405 378/4 |
| 2009/0110152 A1 | 4/2009 | Manzke et al. | |
| 2012/0177171 A1 | 7/2012 | Gutfleisch et al. | |
| 2018/0000432 A1 | 1/2018 | Pruyne | |

FOREIGN PATENT DOCUMENTS

DE    102010026674 A1    1/2012

OTHER PUBLICATIONS

German Office Action for German Application No. 10 2020 206 784.8 dated Jan. 18, 2021.

* cited by examiner

*Primary Examiner* — Courtney D Thomas
(74) *Attorney, Agent, or Firm* — Harness, Dickey & Pierce, P.L.C.

(57) ABSTRACT

A computed tomography device includes, in an embodiment, a gantry including a tunnel-shaped opening, an examination object being introducible into the tunnel-shaped opening for an examination via the computed tomography device; and a radiation protection apparatus to cover the tunnel-shaped opening, the radiation protection apparatus including a first connector and the gantry includes a second connector. In an embodiment, a detachable connection is formable via the first connector and the second connector, to counteract removal of the radiation protection apparatus from the tunnel-shaped opening.

24 Claims, 19 Drawing Sheets

FIG 11
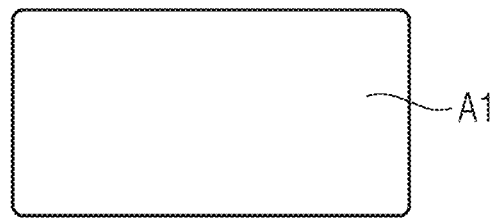
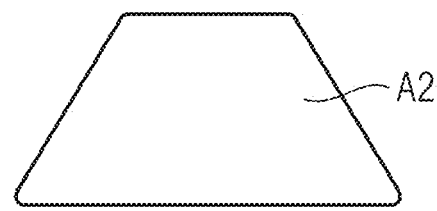
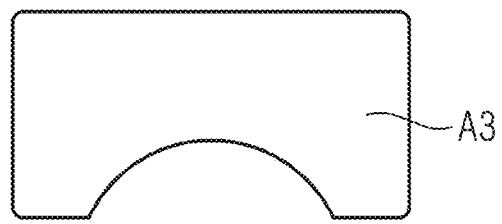
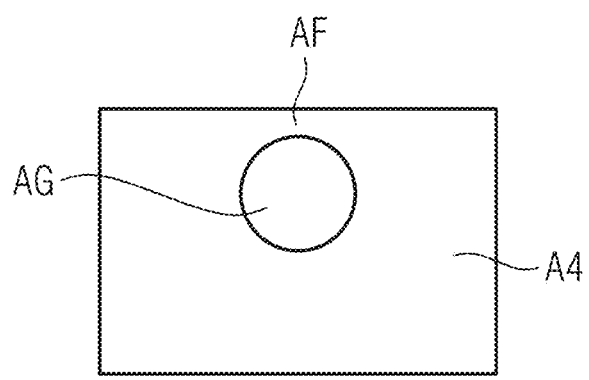

COMPUTED TOMOGRAPHY DEVICE WITH A RADIATION PROTECTION APPARATUS FOR COVERING THE TUNNEL-SHAPED OPENING

PRIORITY STATEMENT

The present application hereby claims priority under 35 U.S.C. § 119 to German patent application number DE 102020206784.8 filed May 29, 2020, the entire contents of which are hereby incorporated herein by reference.

FIELD

Example embodiments of the invention generally relate to a computed tomography device (CT). Example embodiments of the invention further generally relate to a method for an examination of an examination object by way of a computed tomography device.

BACKGROUND

Mobile computed tomography devices are used increasingly in environments which were originally not designed to accommodate a device which emits ionizing scattered radiation. Examples of such environments are intensive care units, operating theaters and treatment rooms, and mobile stroke units. The operator of the computed tomography device and potentially adjacent patients must be protected from the scattered radiation as much as reasonably achievable, cf. the ALARA principle (as much as reasonably achievable).

In order to protect the environment of the computed tomography device from scattered radiation, cladding parts of the computed tomography device can have layers made from a radiation protection material, for instance from lead. Furthermore, measures are required to protect the environment of the computed tomography device from a scattered radiation, which leaves a tunnel-shaped opening of the computed tomography device on a front side or on a rear side of the computed tomography device.

U.S. Pat. No. 8,057,097 B1 discloses a radiation curtain, which is pivotably connected to a scanner, in order to cover at least one side of the opening in the scanner during the scanning process.

SUMMARY

At least one embodiment of the invention enables improved protection of an environment of a computed tomography device from scattered radiation, which leaves a tunnel-shaped opening of the computed tomography device. Further advantageous aspects of embodiments of the invention are taken into consideration in the claims.

At least one embodiment of the invention relates to a computed tomography device, comprising:

a gantry with a tunnel-shaped opening, into which an examination object can be introduced for an examination by way of the computed tomography device; and a radiation protection apparatus for covering the tunnel-shaped opening, in particular for protecting an environment of the computed tomography device from scattered radiation, which leaves the tunnel-shaped opening, wherein the radiation protection apparatus has a first connector, wherein the gantry has a second connector, wherein a detachable connection can be formed via the first connector and the second connector and counteracts a removal of the radiation protection apparatus from the tunnel-shaped opening.

At least one embodiment of the invention further relates to a method for examining an examination object by way of a computed tomography device, wherein the computed tomography device has a gantry with a tunnel-shaped opening, into which the examination object can be introduced for the examination by way of the computed tomography device, and has a radiation protection apparatus for covering the tunnel-shaped opening, wherein the radiation protection apparatus has a first connector, wherein the gantry has a second connector, wherein a detachable connection is formed via the first connector and the second connector and counteracts a removal of the radiation protection apparatus from the tunnel-shaped opening, wherein the gantry has a first gantry part and a second gantry part, wherein the first gantry part has a rotatably supported rotor with a projection data acquisition system, wherein the second gantry part has the second connector and at least one section of the tunnel-shaped opening, wherein the first gantry part is supported so that it can move in relation to the second gantry part, wherein a translational movement of the first gantry part is carried out in relation to the second gantry part, while simultaneously the second gantry part is at rest in relation to the examination object and the radiation protection device is at rest in relation to the examination object and in relation to the at least one section of the tunnel-shaped opening.

At least one embodiment of the invention further relates to a computed tomography device, comprising:

a gantry including a tunnel-shaped opening, an examination object being introducible into the tunnel-shaped opening for an examination via the computed tomography device; and a radiation protection apparatus to cover the tunnel-shaped opening, the radiation protection apparatus including a first connector and the gantry includes a second connector, wherein a detachable connection is formable via the first connector and the second connector, to counteract removal of the radiation protection apparatus from the tunnel-shaped opening.

At least one embodiment of the invention further relates to a method for an examination of an examination object via a computed tomography device, the computed tomography device including a gantry including a tunnel-shaped opening and a radiation protection apparatus to cover the tunnel-shaped opening, the radiation protection apparatus including a first connector and the gantry including a second connector, the gantry including a first gantry part and a second gantry part, the first gantry part including a rotatably supported rotor with a projection data acquisition system and the second gantry part including the second connector and at least one section of the tunnel-shaped opening, the first gantry part being supported to be movable in relation to the second gantry part, the method comprising:

introducing the examination object into the tunnel-shaped opening of the gantry, for the examination via the computed tomography device, wherein a detachable connection is formed via the first connector and the second connector to counteracts a removal of the radiation protection apparatus from the tunnel-shaped opening; and carrying out a translational movement of the first gantry part in relation to the second gantry part, while simultaneously the second gantry part remains at rest in relation to the examination object and while the radiation protection apparatus remains at rest in relation to the examination object and in relation to the at least one section of the tunnel-shaped opening.

BRIEF DESCRIPTION OF THE DRAWINGS

The invention will be explained below on the basis of example embodiments with reference to the accompanying figures. The illustrations in the figures are schematic, greatly simplified and not necessarily to scale.

In the drawings:

FIG. 11 shows a number of examples of a radiation curtain.

DETAILED DESCRIPTION OF THE EXAMPLE EMBODIMENTS

Figure 1:
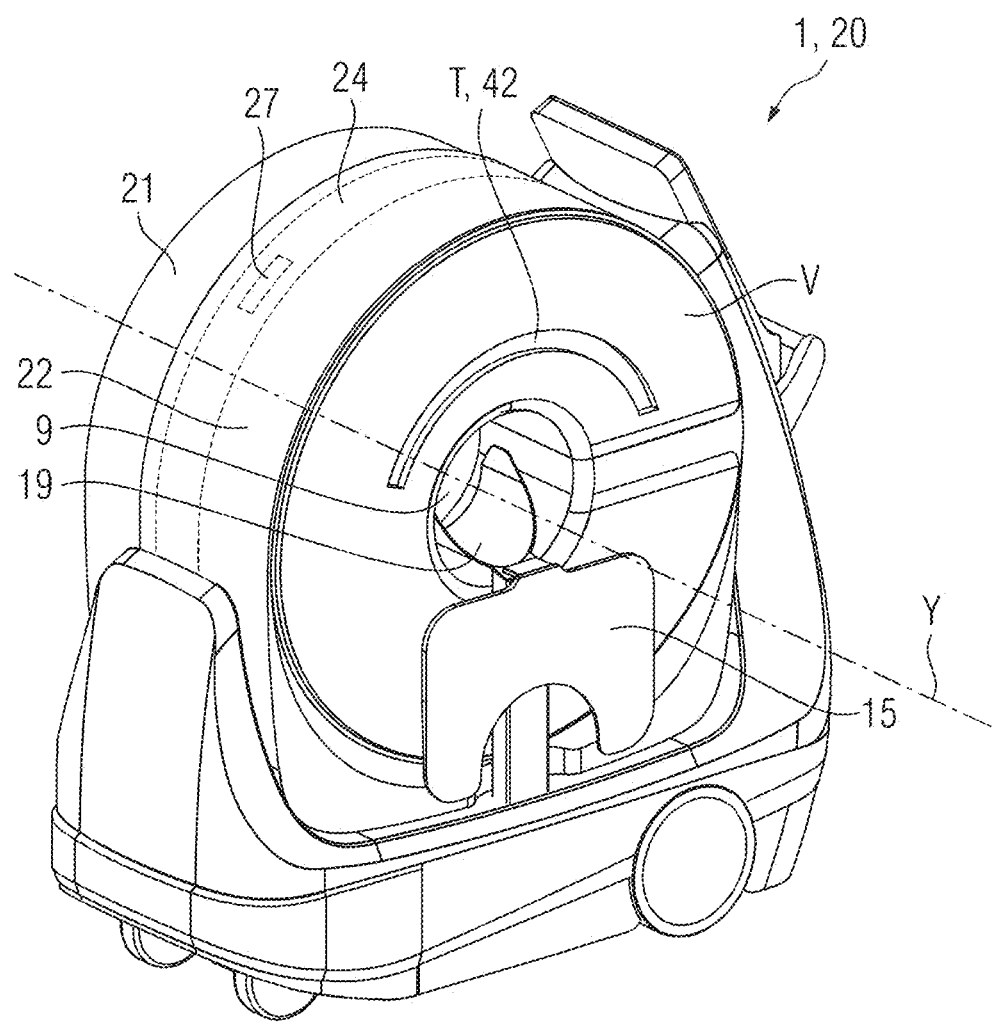
FIG. 1 shows a computed tomography device for an examination of a head of a patient.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. At least one embodiment of the present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment of the invention relates to a computed tomography device, comprising:

a gantry with a tunnel-shaped opening, into which an examination object can be introduced for an examination by way of the computed tomography device; and a radiation protection apparatus for covering the tunnel-shaped opening, in particular for protecting an environment of the computed tomography device from scattered radiation, which leaves the tunnel-shaped opening, wherein the radiation protection apparatus has a first connector, wherein the gantry has a second connector, wherein a detachable connection can be formed via the first connector and the second connector and counteracts a removal of the radiation protection apparatus from the tunnel-shaped opening.

The radiation protection apparatus can be based in particular on at least one radiation protection material, for instance lead, in particular so that the scattered radiation of the computed tomography device is largely absorbed in the radiation protection apparatus and is as a result fundamentally prevented from penetrating the radiation protection apparatus.

The examination object can be a head of a patient, for instance. The computed tomography device can be embodied in particular as a head computed tomography device and/or as a mobile computed tomography device.

The second connector can be embodied to correspond in particular to the first connector. The detachable connection can be a magnetic connection and/or a form-fit connection, for instance. The detachable connection can be a plug connection and/or detachable without using a tool, for instance.

One embodiment provides that the gantry has a first gantry part and a second gantry part, wherein the first gantry part has a rotatably supported rotor with a projection data acquisition system, wherein the second gantry part has the second connector and at least one section of the tunnel-shaped opening, wherein the first gantry part is supported movably in relation to the second gantry part, that a translational movement, in particular along a system axis of the computed tomography device, of the first gantry part can be carried out in relation to the second gantry part, while at the same time the second gantry part is at rest in relation to the examination object and the radiation protection apparatus is at rest in relation to the examination object and in relation to the at least one section of the tunnel-shaped opening when the detachable connection is formed via the first connector and the second connector.

The projection data acquisition system can have in particular an x-ray radiation source and an x-ray radiation detector which interacts with the x-ray radiation source.

This enables an optimal coverage of the tunnel-shaped opening during the entire examination, particularly without leakages possibly occurring between the radiation protection apparatus and the gantry, through which the scattered radiation can enter the environment.

With conventional computed tomography devices, during the examination the entire gantry moves in relation to the patient along a longitudinal direction of the patient. A radiation protection apparatus connected with the cladding of such a gantry therefore likewise moves in relation to the patient during the examination and could damage wires and/or devices connected to the patient.

Furthermore, a position of the radiation curtain in relation to the tunnel-shaped opening can be changed under the influence of the patient moving in relation to the radiation curtain, so that leakages occur between the radiation protection apparatus and the gantry, through which scattered radiation can enter the environment.

One embodiment provides that the first connector has at least one ferromagnetic region and the second connector has at least one magnet.

One further embodiment provides that the first connector has at least one magnet and the second connector has at least one ferromagnetic region.

The detachable connection can be formed for instance by a magnetic interaction, in particular a magnetic force of attraction, between the at least one magnet and the at least one ferromagnetic region.

One embodiment provides that the radiation protection apparatus has a radiation curtain and a rail for suspending the radiation curtain so that it can move and/or can be mounted along the rail, wherein the rail has the first connector.

One embodiment provides that the gantry has a cladding, wherein the cladding has a recess, in which the rail can be received in a form-fit manner, wherein the second connector is arranged in a region of the recess so that the detachable connection counteracts a removal of the rail from the recess (T) when the rail is received in the recess in a form-fit manner.

The radiation curtain can in particular have a flexible two-dimensional radiation protection material. The flexible two-dimensional radiation protection material can be based at least partially on lead, for instance, and/or have at least a lead-free radiation protection material.

For instance, the rail can be held on the gantry, in particular in the recess for the form-fit receiving of the rail, via a magnetically detachable connection. The second connector, which has the at least one magnet, can be integrated into a front side of the gantry, in particular above the tunnel-shaped opening.

The at least one magnet is dimensioned sufficiently strongly to hold the radiation protection apparatus with the rail and the radiation curtain and in particular to prevent the radiation protection apparatus from inadvertently falling onto the patient. It is also possible to press the rail against a flat region of the cladding, solely via a magnetic attraction force, so that the static friction between the rail and the flat region of the cladding is sufficiently strong to hold the rail on the flat region of the cladding.

If necessary, for instance for cleaning and/or sterilization purposes, the rail can be removed from the gantry without using a tool, by overcoming the magnetic attraction force.

For instance, the rail can be essentially transparent for visible light, for instance, and/or be produced essentially from lead glass. The rail therefore contributes to protecting the environment from scattered radiation leaving the tunnel-shaped opening, and at the same time enables visible light from an environment of the computed tomography device to penetrate the tunnel-shaped opening. As a result, a brightness in the tunnel-shaped opening can be improved without additional electrical illumination elements.

One embodiment provides that the radiation protection apparatus has a radiation curtain and a sliding carriage, wherein the radiation curtain is connected to the sliding carriage and is mounted along the sliding carriage, wherein the gantry has a rail for supporting the sliding carriage so that it can move along the rail, wherein the sliding carriage has the first connector, wherein the rail has the second connector.

The weight of the radiation curtain is uniformly transferred to the rail by using the sliding carriage. The effort the user of the computed tomography device has to expend to pull the radiation curtain in order to cover the tunnel-shaped opening with the radiation curtain can therefore be reduced.

Furthermore, it is possible for the user to pull the radiation curtain with just one hand, while the other hand secures the patient and/or wires connected to the patient. This additionally increases the safety of the patient.

One embodiment provides that the radiation curtain is detachably connected to the sliding carriage.

The radiation curtain can therefore be removed from the sliding carriage, if necessary, for cleaning and/or sterilization purposes.

One embodiment provides that the radiation curtain has a lead-glass window.

The lead-glass window can be arranged in particular in a top region of the radiation curtain. The lead-glass window can be rectangular or round, for instance, or have another shape.

A user of the computed tomography device can observe the patient, for instance the face of the patient, through the lead-glass window, particularly if the radiation curtain is pulled and covers the tunnel-shaped opening.

One embodiment provides that the radiation curtain has a strip-shaped region made from a flexible radiation protection material which is arranged between the lead-glass window and the sliding carriage.

As a result, an orientation of the lead-glass window can be better adjusted to the requirements of the user and/or the examination.

One embodiment provides
that the radiation protection apparatus has a radiation protection body, wherein the gantry has a cladding, wherein the cladding has a recess, in which the radiation protection body can be received in a form-fit manner, wherein the radiation protection body has the first connector, wherein the second connector is arranged in a region of the recess such that the detachable connection counteracts a removal of the radiation protection body from the recess when the radiation protection body is received in the recess in a form-fit manner.

One embodiment provides
that the tunnel-shaped opening extends along a system axis of the computed tomography device wherein the radiation protection body extends in a two-dimensional manner in a plane of the radiation protection body, wherein the plane of the radiation protection body is at right angles to the system axis of the computed tomography device when the radiation protection body is received in the recess in a form-fit manner.

In particular, the recess, in which the radiation protection body can be received in a form-fit manner, can be embodied in a stepped manner and/or so as to run around the system axis of the computed tomography device. In particular, the radiation protection body may be embodied in a plate-shaped manner. The system axis of the computed tomography device can be an axis of rotation of the rotor of the computed tomography device, for instance. The rotor of the computed tomography device can be supported so that it can rotate in particular about the axis of rotation of the rotor of the computed tomography device, in particular in relation to the tunnel-shaped opening and/or in relation to the second gantry part.

One embodiment provides
that the radiation protection body has a lead-glass panel and a holding frame for the lead-glass panel, wherein the lead-glass panel is fixed in the holding frame, wherein the holding frame can be received in the recess in a form-fit manner and forms the first connector.

In particular, the holding frame can be ferromagnetic and/or form the first connector.

The lead-glass panel can be received in the holding frame in a form-fit manner, for instance, and/or glued to the holding frame. The holding frame can be essentially annular, in particular annular, for instance.

Visible light from its environment of the computed tomography device can penetrate the tunnel-shaped opening through the lead-glass panel.

As a result, a brightness in the tunnel-shaped opening can be improved without additional electrical illumination elements. In this way, patient comfort and his/her willingness to cooperate can be improved, in particular.

One embodiment provides
that the radiation protection body is embodied so that a subregion of the tunnel-shaped opening is not covered by the radiation protection body, when the radiation protection body is received in the recess in a form-fit manner, wherein the radiation protection apparatus has a radiation curtain for covering the subregion of the tunnel-shaped opening, wherein the radiation curtain is connected, in particular detachably connected, to the radiation protection body so that the radiation curtain covers the subregion of the tunnel-shaped opening when the radiation protection body is received in the recess in form-fit manner.

In particular, provision can be made for the radiation curtain not to cover the subregion of the tunnel-shaped opening, which is not covered by the radiation protection body, in an air-tight manner.

An air exchange between the tunnel-shaped opening and an environment of the computed tomography device can therefore take place through the subregion of the tunnel-shaped opening which is not covered by the radiation protection body. As a result, more complicated solutions for the air exchange can be avoided and patient comfort and his/her willingness to cooperate can be further increased.

One embodiment provides that a hand, in particular a hand of a user of the computed tomography device, can be introduced at least partially into the subregion of the tunnel-shaped opening so that an edge region of the radiation protection body adjoining the subregion of the tunnel-shaped opening can be gripped with the hand when the radiation protection body is received in the recess in a form-fit manner.

One embodiment provides that the radiation protection apparatus has a connecting part, which is connected to the radiation protection body and is embodied to receive a tensile force for removing the radiation protection body from the recess, when the radiation protection body is received in the recess in a form-fit manner.

The connecting part can be embodied as a loop, for instance.

In particular, provision can be made for the connecting part to be arranged opposite the subregion of the tunnel-shaped opening, in respect of a center of gravity of the radiation protection body, the subregion not being covered by the radiation protection body.

In particular, provision can be made for the connecting part to be arranged in an upper region of the radiation protection body and for the subregion of the tunnel-shaped opening, which is not covered by the radiation protection body, to be arranged in a lower region of the radiation protection body when the radiation protection body is received in the recess in a form-fit manner.

A user can therefore simultaneously hold the radiation protection body, which may be several kilograms heavy, with one hand on the subregion on the edge region of the radiation protection body adjoining the subregion of the tunnel-shaped opening and with the other hand on the connecting part. As a result, safety when receiving and removing the radiation protection body is additionally increased.

The gantry of a computed tomography device typically has a support construction, on which in particular components of the projection data acquisition system, in particular the x-ray radiation source and/or the x-ray radiation detector, are arranged. The support construction of the gantry typically has a high rigidity and stability of this type, so that the components of the acquisition unit can be arranged in a geometry defined sufficiently for the imaging both in relation to one another and also in relation to a region to be mapped.

With a computed tomography device, the gantry typically has a support frame and a rotor supported rotatably in relation to the support frame, wherein the x-ray radiation source and the x-ray radiation detector are arranged on the rotor. The gantry can optionally have a tilting frame supported tiltably in relation to the supporting frame, wherein the rotor is arranged on the tilting frame.

At least one embodiment of the invention further relates to a method for examining an examination object by way of a computed tomography device, wherein the computed tomography device has a gantry with a tunnel-shaped opening, into which the examination object can be introduced for the examination by way of the computed tomography device, and has a radiation protection apparatus for covering the tunnel-shaped opening, wherein the radiation protection apparatus has a first connector, wherein the gantry has a second connector, wherein a detachable connection is formed via the first connector and the second connector and counteracts a removal of the radiation protection apparatus from the tunnel-shaped opening, wherein the gantry has a first gantry part and a second gantry part, wherein the first gantry part has a rotatably supported rotor with a projection data acquisition system, wherein the second gantry part has the second connector and at least one section of the tunnel-shaped opening, wherein the first gantry part is supported so that it can move in relation to the second gantry part, wherein a translational movement of the first gantry part is carried out in relation to the second gantry part, while simultaneously the second gantry part is at rest in relation to the examination object and the radiation protection device is at rest in relation to the examination object and in relation to the at least one section of the tunnel-shaped opening.

In particular, provision can be made for the examination object to be a head of a patient and/or for the translational movement of the first gantry part to be carried out in relation to the second gantry part, while the radiation protection apparatus simultaneously makes contact with the patient.

In particular, provision can be made for the translational movement to be carried out along a system axis of the computed tomography device. Here the system axis of the computed tomography device can be an axis of rotation of the rotor of the computed tomography device, for instance.

Within the scope of the invention, features, which are described in respect of different embodiments of the invention and/or different claim categories (method, use, apparatus, system, arrangement etc.) are combined to form further embodiments of the invention.

For instance, a claim, which relates to an apparatus, can also be further developed with features, which are described or claimed in conjunction with a method, and vice versa. Functional features of a method can be carried out here by correspondingly embodied representational components. In addition to the embodiments of the invention expressly described in this application, many further embodiments of the invention are conceivable, at which the person skilled in the art can arrive without departing from the scope of the invention, as specified by the claims.

The expression "on the basis of" or "based upon" can be understood in the context of the present application in particular in the sense of the expression "by using". In particular, a formulation as a result of which a first feature is created (alternatively: determined, specified, etc.) on the basis of a second feature does not preclude that the first feature can be created (alternatively: determined, specified, etc.) on the basis of a third feature.

FIG. 1 shows a computed tomography device 1 for an examination of a head O of a patient 13.

The computed tomography device 1 is embodied as a mobile computed tomography device and has a gantry 20 with a tunnel-shaped opening 9, into which an examination object O can be introduced for an examination by way of the computed tomography device 1. The examination object O is the head of the patient 13. The head of the patient 13 is received in the head cap 19 for the examination via the computed tomography device 1. The gantry 20 has a cladding V, wherein the cladding V has a recess T, in which the rail R can be received in a form-fit manner.

The gantry 20 has a first gantry part 21 and a second gantry part 22, wherein the first gantry part 21 has a rotor 24 supported rotatably with a projection data acquisition system 27, wherein the second gantry part 22 has the second connector 42 and at least one section of the tunnel-shaped opening 9. The projection data acquisition system 27 has an x-ray radiation source and an x-ray radiation detector which interacts with the x-ray radiation source. On account of this arrangement of the first gantry part 21 in relation to the second gantry part 22, the gantry 20 can be referred to as the telescopic gantry.

The first gantry part 21 is supported movably in relation to the second gantry part 22 so that a translational movement, in particular along the system axis Y of the computed tomography device 1, of the first gantry part 21 can be carried out in relation to the second gantry part 22, while at the same time the second gantry part 22 is at rest in relation to the examination object O and the radiation protection apparatus 4 is at rest in relation to the examination object O and in relation to the at least one section of the tunnel-shaped opening 9 when the detachable connection is formed via the first connector 41 and the second connector 42.

The gantry 20 has a cladding V, wherein the cladding V has a recess T, in which the rail R can be received in a form-fit manner.

Figure 2:
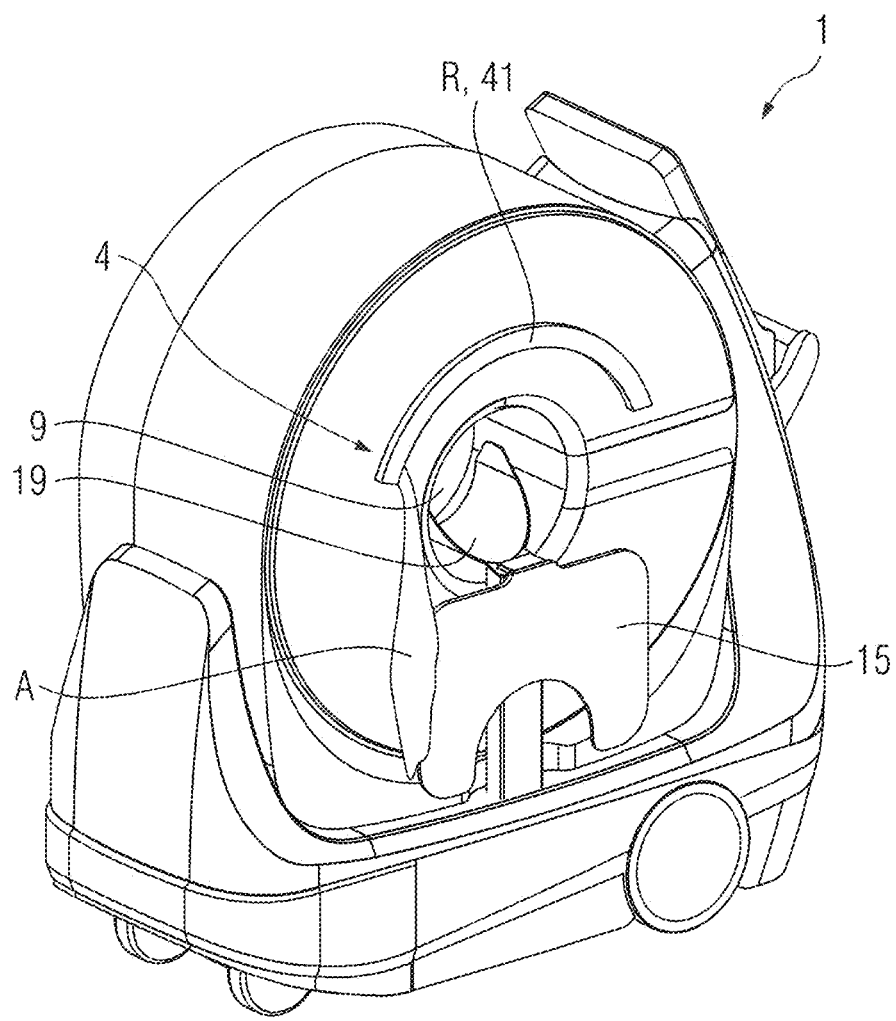
FIG. 2 shows a computed tomography device with a radiation curtain suspended on a rail in a first view.

FIG. 2 shows the computed tomography device 1 with a radiation curtain A suspended on a rail R in a first view.

Figure 3:
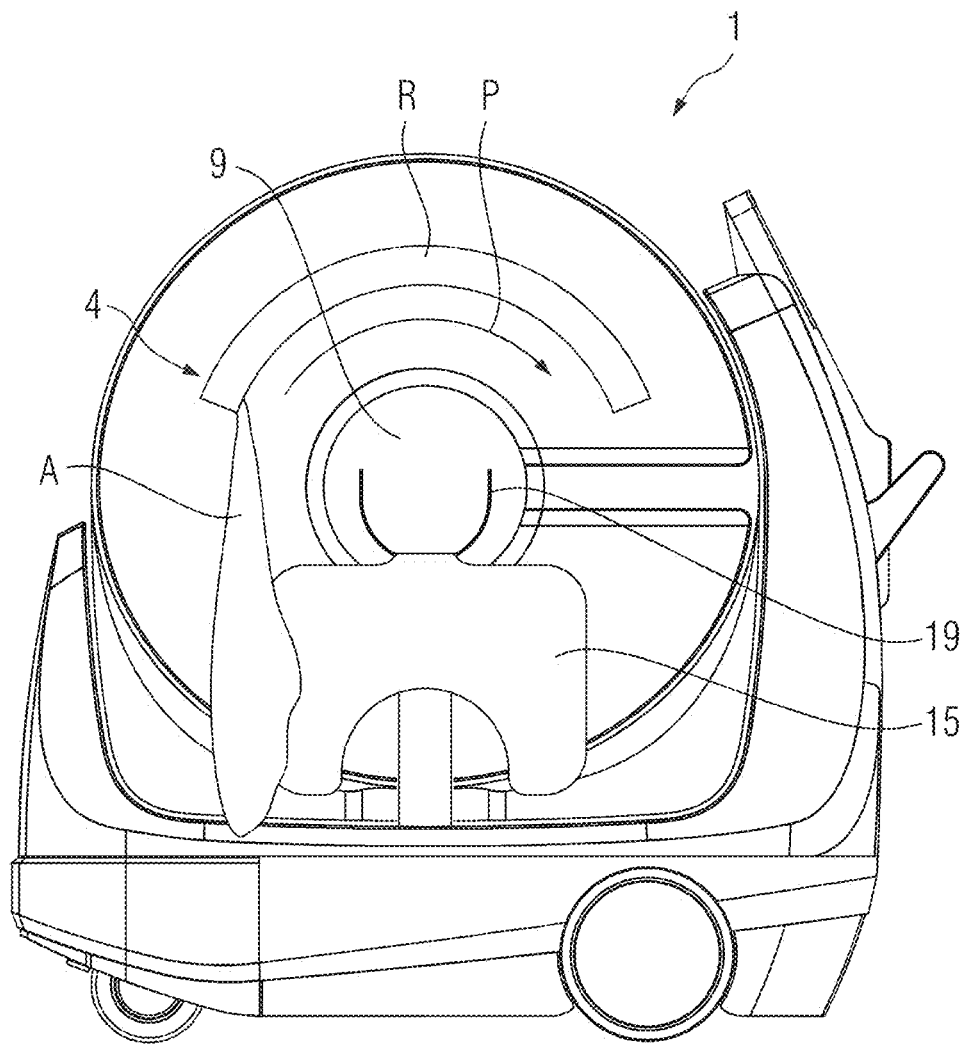
FIG. 3 shows a computed tomography device with a radiation curtain suspended on a rail in a second view.

FIG. 3 shows the computed tomography device 1 with the radiation curtain A suspended on a rail R in a second view.

Figure 4:
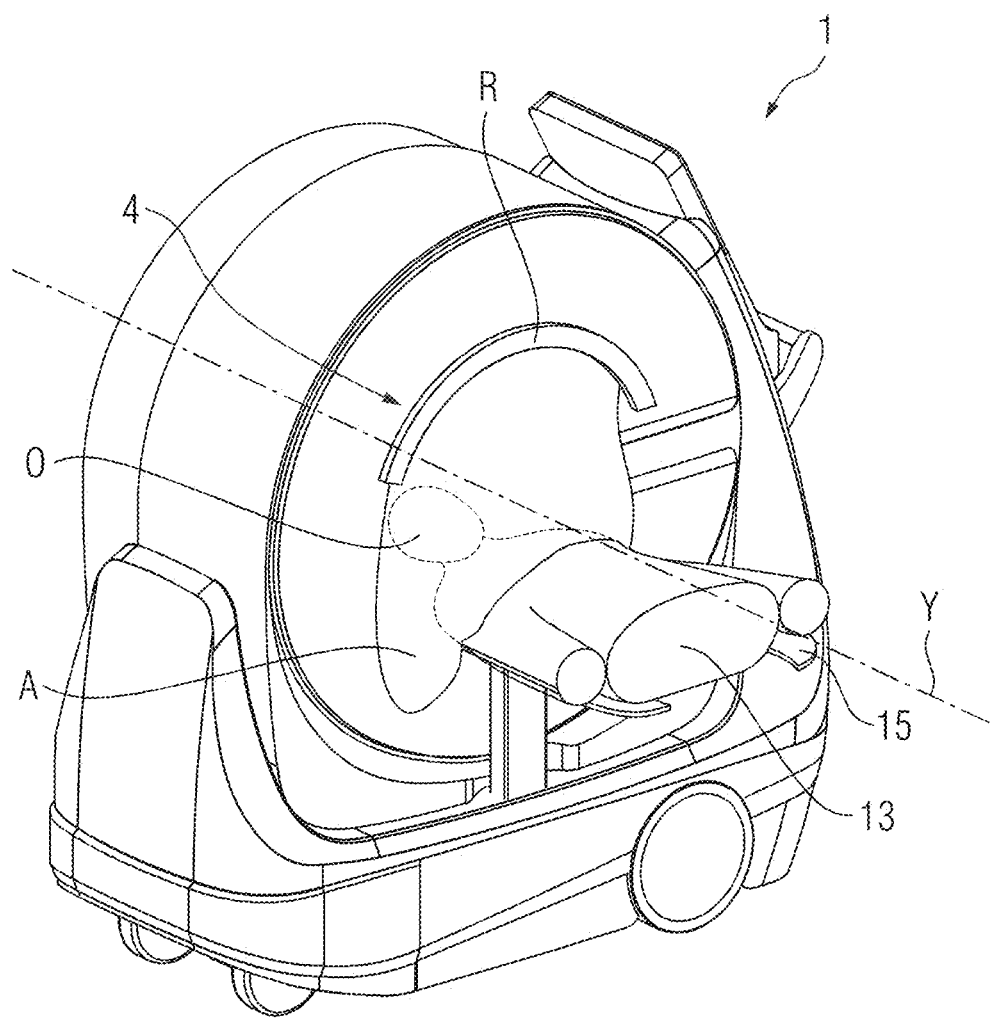
FIG. 4 shows a computed tomography device with a radiation curtain suspended on a rail during an examination of a head of a patient.

FIG. 4 shows the computed tomography device 1 with the radiation curtain A suspended on the rail R during an examination of the head O of the patient 13.

The computed tomography device 1 has a radiation protection apparatus 4 for covering the tunnel-shaped opening 9 to protect an environment of the computed tomography device 1 from scattered radiation, which leaves the tunnel-shaped opening 9.

The radiation protection apparatus 4 has the first connector 41. The gantry 20 has the second connector 42. A detachable connection can be formed via the first connector 41 and the second connector 42 and counteracts a removal of the radiation protection apparatus 4 from the tunnel-shaped opening 9.

The radiation protection apparatus 4 has a radiation curtain A and a rail R for suspending the radiation curtain A so that it can be moved and/or mounted along the rail R, wherein the rail R has the first connector 41.

The first connector 41 has at least one ferromagnetic region and the second connector 42 has at least one magnet. The second connector 42 is arranged in a region of the recess T so that the detachable connection is embodied as a detachable magnetic connection and counteracts a removal of the rail R from the recess T when the rail R is received in the recess T in a form-fit manner.

The upper body of the patient 13 is supported on the patient support unit 15 of the gantry 20. The remaining part of the patient 13 is supported on a support plate, not shown, which connects to the patient support unit 15 in the longitudinal direction of the patient 13.

Figure 5:
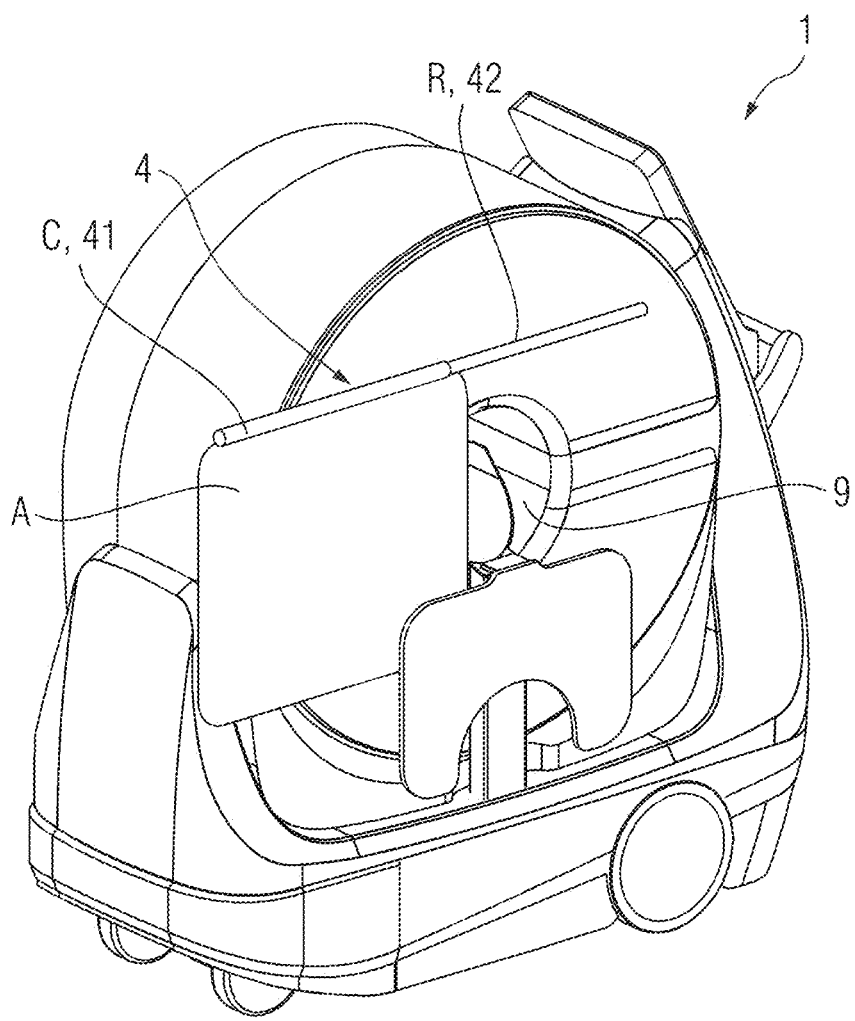
FIG. 5 shows a computed tomography device, having a radiation curtain, a sliding carriage and a rail in a first operating state of the radiation protection apparatus.
Figure 6:
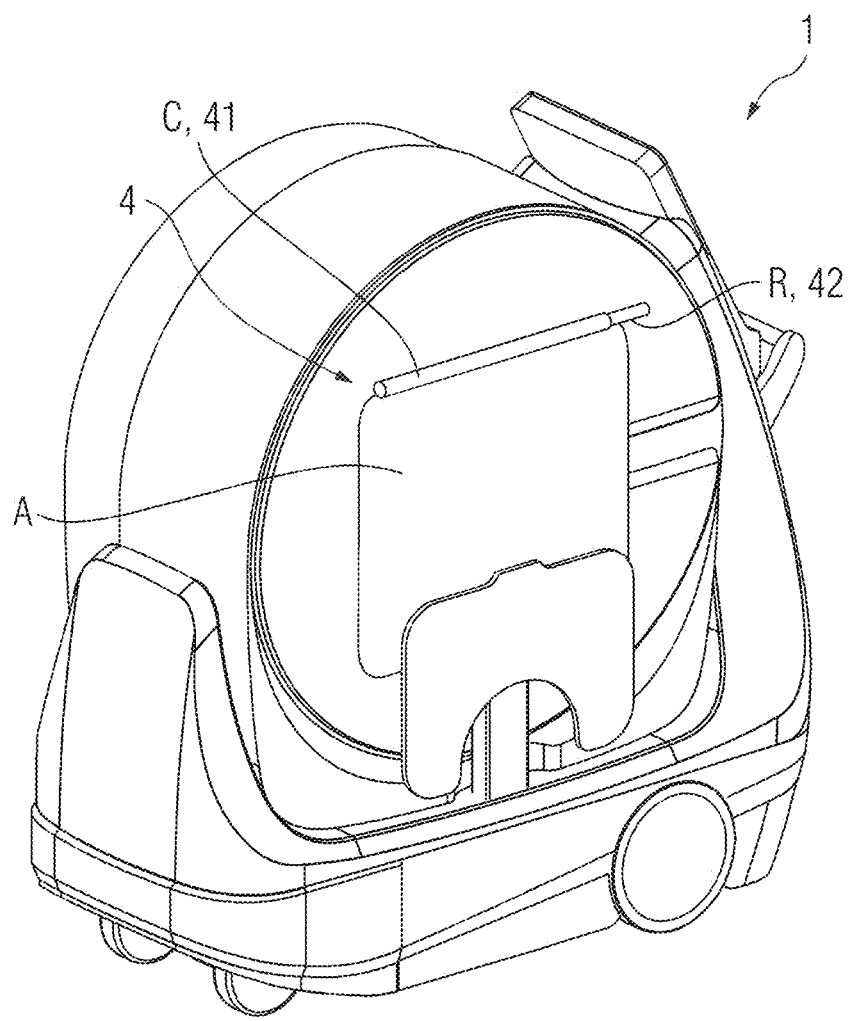
FIG. 6 shows a computed tomography device, having a radiation curtain, a sliding carriage and a rail in a second operating state of the radiation protection apparatus.

FIG. 5 shows a computed tomography device 1, having a radiation curtain A, a sliding carriage C and a rail R in a first operating state of the radiation protection apparatus 4. FIG. 6 shows the computed tomography device 1, having a radiation curtain A, a sliding carriage C and a rail R in a second operating state of the radiation protection apparatus 4.

The radiation protection apparatus 4 has a radiation curtain A and a sliding carriage C, wherein the radiation curtain A is connected to the sliding carriage C and mounted along the sliding carriage C. The gantry 20 has a rail R for supporting the sliding carriage C so that it can be moved along the rail R. The sliding carriage C has the first connector 41. The rail R has the second connector 42. The rail R is arranged above the tunnel-shaped opening 9.

Figure 7:
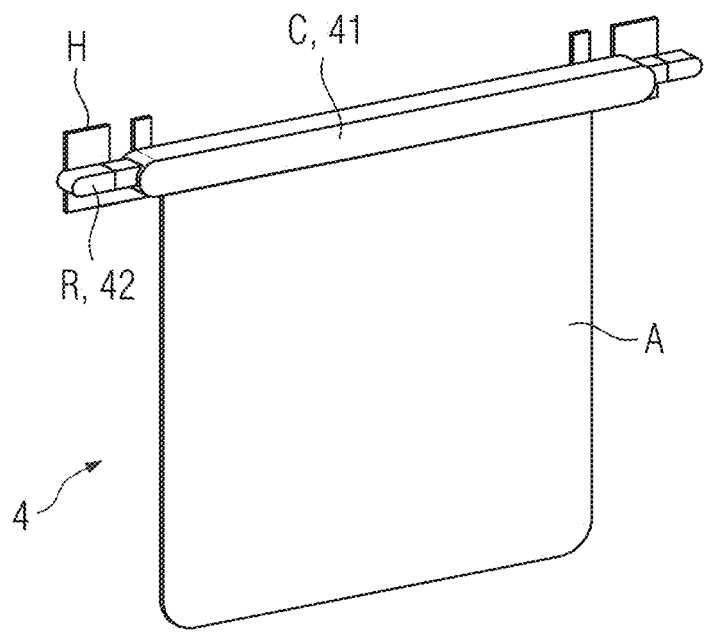
FIG. 7 shows a radiation protection apparatus with a sliding carriage on a rail in a first view.
Figure 8:
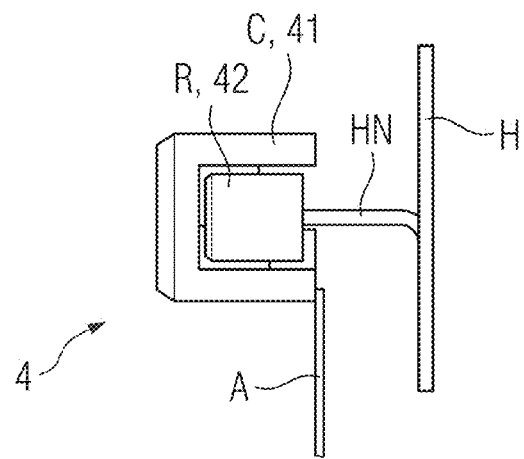
FIG. 8 shows a radiation protection apparatus with a sliding carriage on a rail in a second view.

FIG. 7 shows a radiation protection apparatus 4 with the sliding carriage C on a rail R in a first view. FIG. 8 shows a radiation protection apparatus 4 with the sliding carriage C on a rail R in a second view.

The radiation curtain A is detachably connected to the sliding carriage C. The rail R can be connected to the cladding V via a rail holder H. The rail holder H can be screwed to the cladding V, for instance, and have through holes corresponding thereto. This enables a very fixed and robust holding of the rail R on the cladding.

Furthermore, this solution can be flexibly adjusted to different embodiments of the rail R, of the sliding carriage C and of the radiation curtain A, if necessary, particularly without complicated changes to the cladding V or to the rail holder H. Alternatively, it is also possible for the rail R to be connected with a support structure of the gantry 20, which is covered by the cladding V, through corresponding openings in the cladding V.

The rail holder H and the rail R can be produced in each case from an easily sterilizable material, for instance stainless steel.

Figure 9:
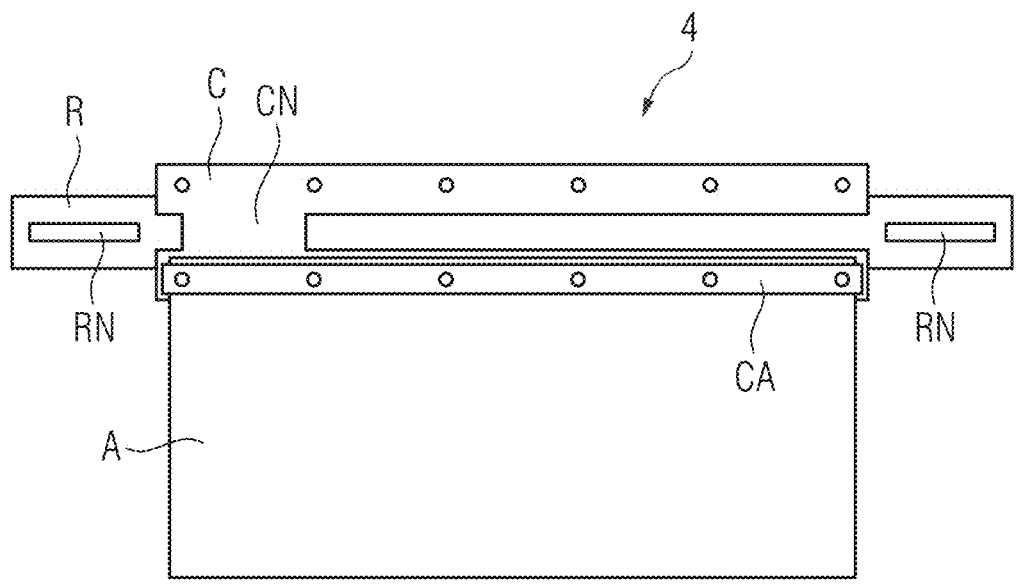
FIG. 9 shows a radiation protection apparatus with a sliding carriage on a rail in a third view.

FIG. 9 shows a radiation protection apparatus 4 with a sliding carriage C on a rail C in a third view.

The sliding carriage C can be easily detachably connected to the rail R without using tools. This enables a simple cleaning and sterilization.

The sliding carriage C is detachably connected to the rail R with a secure locking mechanism; this prevents the sliding carriage C from inadvertently detaching from the rail R and the sliding carriage C from falling down.

The sliding carriage C is restricted in its movement along the rail R between two extreme positions on account of this construction. The holding rods HN of the rail holder H are inserted into the rail R in recesses RN provided herefor.

The sliding carriage C has a blocking element CN, the form fit of which with in each case one of the holding rods HN prevents the sliding carriage C from moving out beyond the extreme positions.

Figure 10:
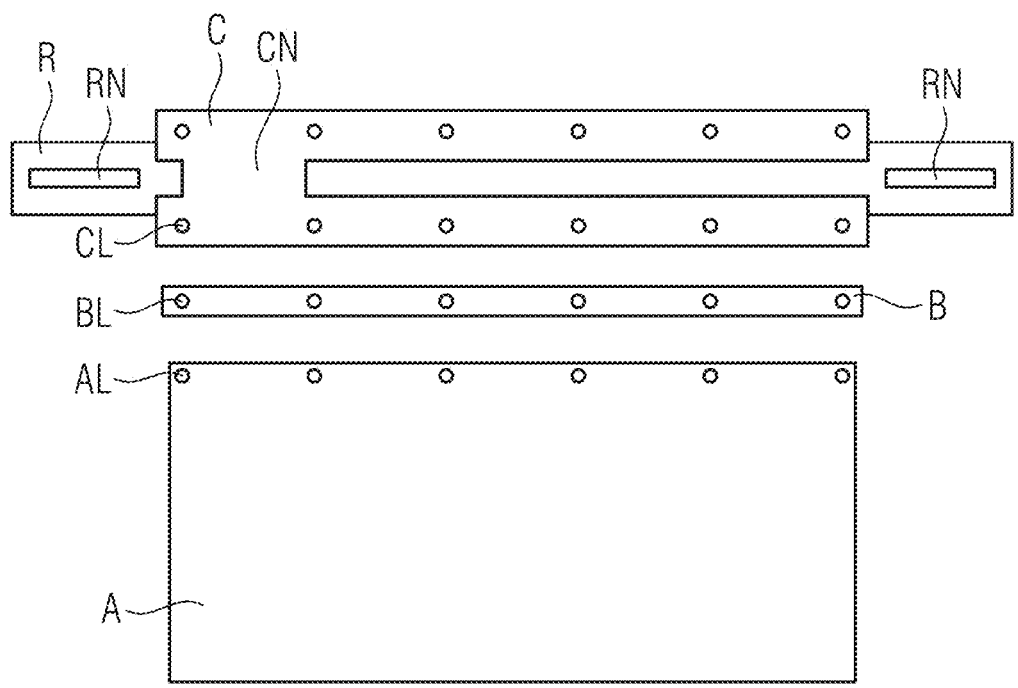
FIG. 10 shows an arrangement with a radiation protection curtain, a sliding carriage and a rail.

FIG. 10 shows an arrangement with a radiation curtain A, a sliding carriage C and a rail R.

The radiation curtain A can be detachably connected to the sliding carriage C, for instance, via clipping on or by trapping a section of the radiation curtain A provided for this purpose. To this end, the connecting elements CL are provided on the sliding carriage C, AL, on the radiation curtain A and optionally further connecting elements BL.

FIG. 11 shows a number of examples of a radiation curtain. The radiation curtain A1 is rectangular. The radiation curtain A2 is trapezoid. The radiation curtain A3 has a cut-out. The radiation curtain A4 has a lead-glass window AG and a strip-shaped region AF made from a flexible radiation protection material, which is arranged between the lead-glass window AG and the sliding carriage C.

Figure 12:
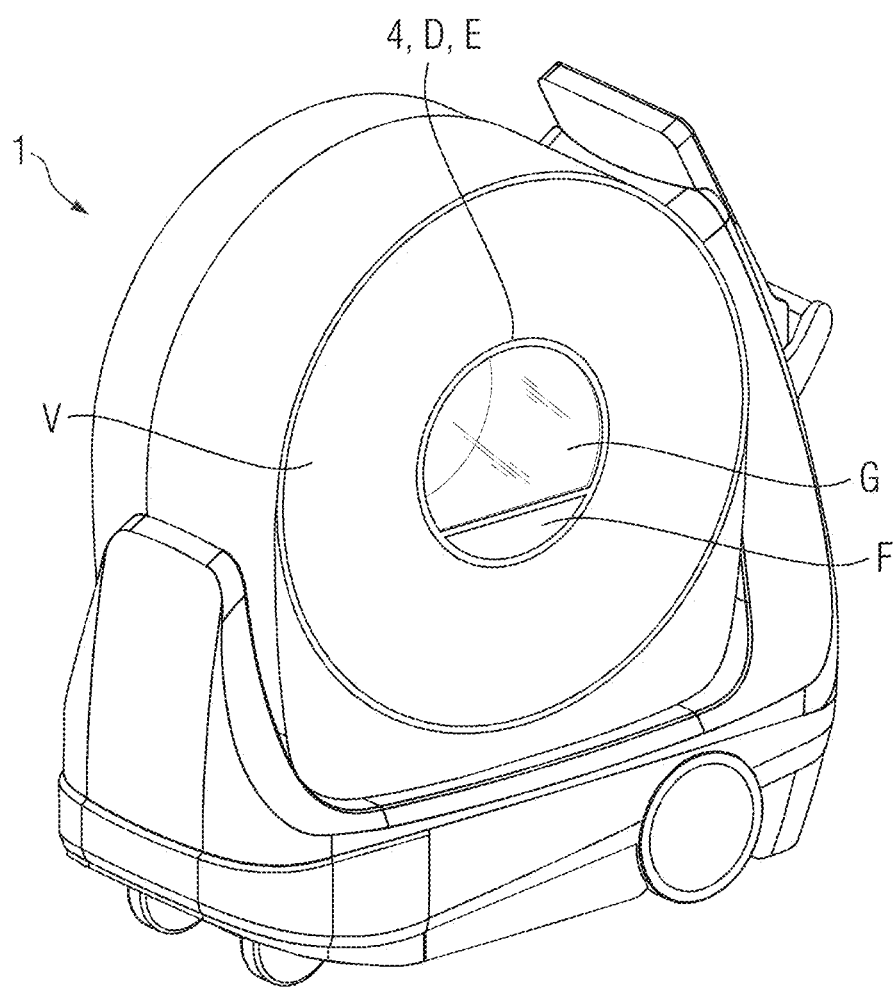
FIG. 12 shows a computed tomography device, having a radiation protection apparatus with a radiation protection body.

FIG. 12 shows a computed tomography device 1, having a radiation protection apparatus 4 with a radiation protection body D. The radiation protection apparatus 4 is arranged on a rear side of the computed tomography device 1.

The radiation protection apparatus 4 has the radiation protection body D, wherein the gantry 20 has a cladding V, wherein the cladding V has a recess W, in which the radiation protection body D can be received in a form-fit manner, wherein the radiation protection body D has the first connector 41.

The second connector 42 is arranged in a region of the recess W such that the detachable connection counteracts a removal of the radiation protection body D from the recess W when the radiation protection body D is received in the recess W in a form-fit manner.

The radiation protection body D is embodied so that a subregion 9F of the tunnel-shaped opening 9 is not covered by the radiation protection body D when the radiation protection body D is received in the recess W in a form-fit manner.

The radiation protection apparatus 4 has a radiation curtain F for covering the subregion 9F of the tunnel-shaped opening 9, wherein the radiation curtain F is connected to the radiation protection body D, in particular detachably connected, so that the radiation curtain F covers the subregion 9F of the tunnel-shaped opening 9 when the radiation protection body D is received in the recess W in a form-fit manner.

Figure 13:
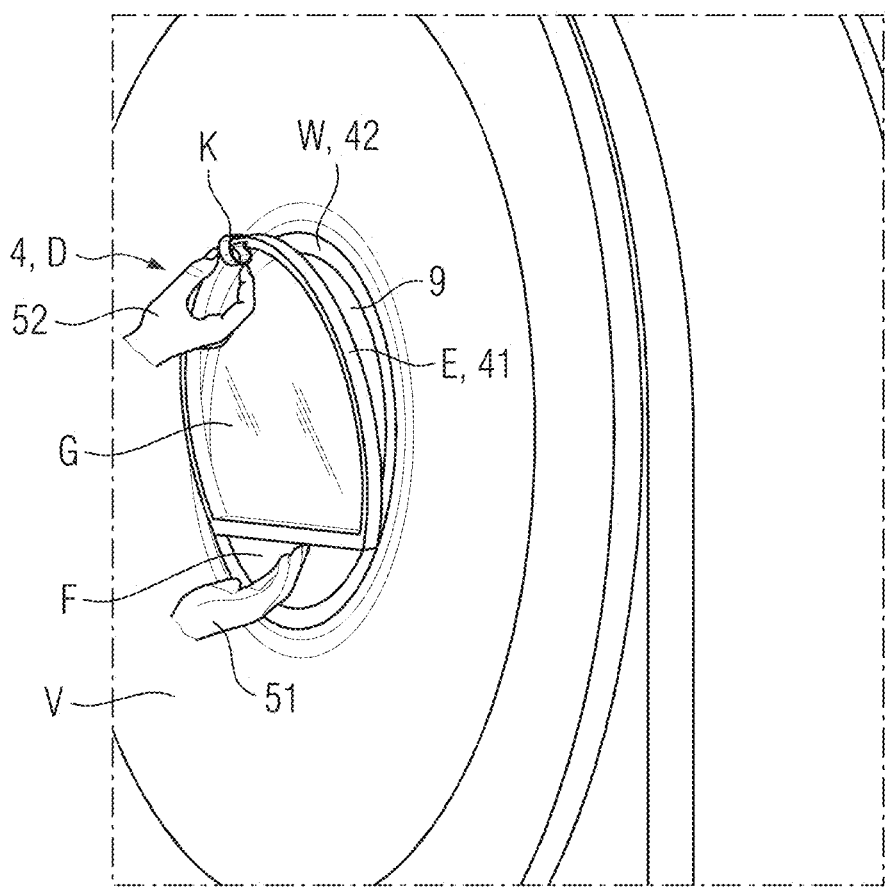
FIG. 13 shows a computed tomography device upon removal of a radiation protection apparatus, which has a radiation protection body, from the tunnel-shaped opening.

FIG. 13 shows the computed tomography device 1 upon removal of the radiation protection apparatus 4, which has a radiation protection body D, from the tunnel-shaped opening 9.

A hand 51 can be introduced at least partially into the subregion 9F of the tunnel-shaped opening 9 so that an edge region of the radiation protection body D adjoining the subregion 9F of the tunnel-shaped opening 9 can be gripped with the hand 51, when the radiation protection body D is received in the recess W in a form-fit manner.

The radiation protection apparatus 4 has a connecting part K in the form of a loop, which is connected to the radiation protection body D and is embodied to receive a tensile force in order to remove the radiation protection body D from the recess W, when the radiation protection body D is received in the recess W in a form-fit manner. The tensile force for removing the radiation protection body D from the recess W can be exerted with the other hand 52, for instance.

The radiation protection body D has a lead-glass panel G and a holding frame E for the lead-glass panel G, wherein the lead-glass panel G is fixed in the holding frame E, wherein the holding frame E can be received in the recess W in a form-fit manner and forms the first connector 41.

Figure 14:
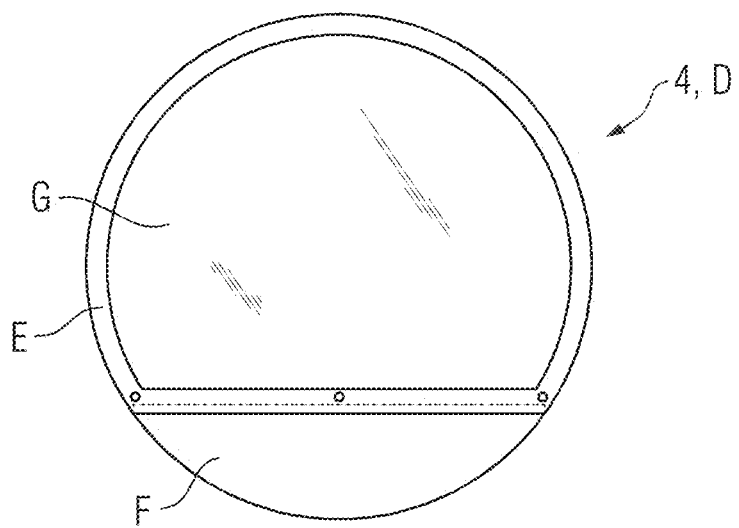
FIG. 14 shows a first example of a radiation protection apparatus with a radiation protection body and a radiation curtain.

FIG. 14 shows a first example of a radiation protection apparatus 4 with a radiation protection body D and a radiation curtain F.

Figure 15:
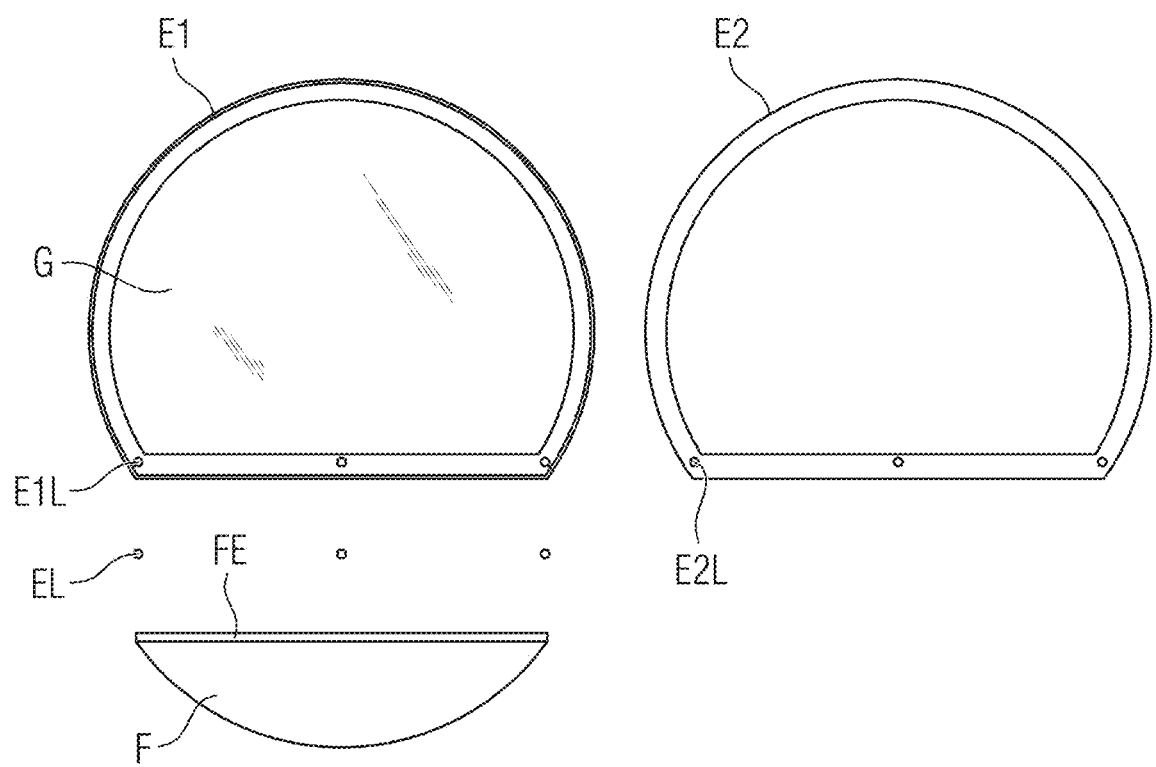
FIG. 15 shows an arrangement with a number of components of a radiation protection body and a radiation curtain.

FIG. 15 shows an arrangement with a number of components E1, E2 of the radiation protection body D and a radiation curtain F.

The components E1 and E2 of the radiation protection body D can be connected with one another via the connecting elements E1, E1L and E2L so that they trap the lead-glass panel G and a section FE of the radiation curtain F which is provided herefor.

Figure 16:
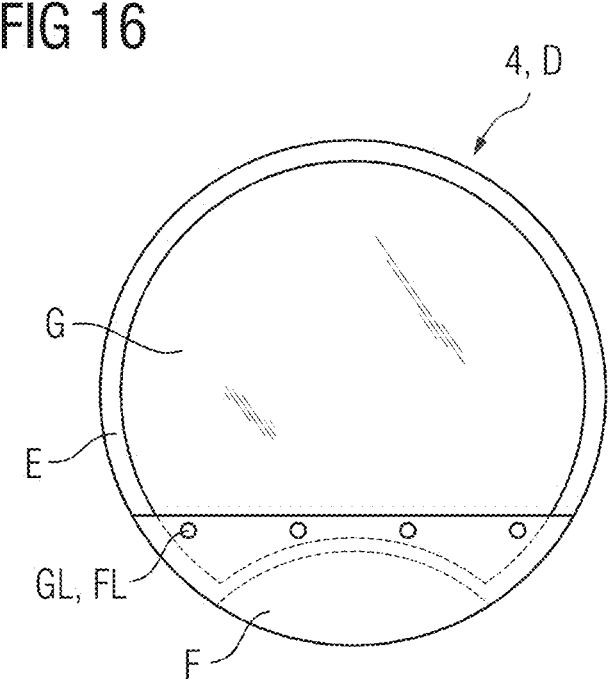
FIG. 16 shows a second example of a radiation protection apparatus with a radiation protection body and a radiation curtain.

FIG. 16 shows a second example of a radiation protection apparatus 4 with a radiation protection body D and a radiation curtain F.

Figure 17:
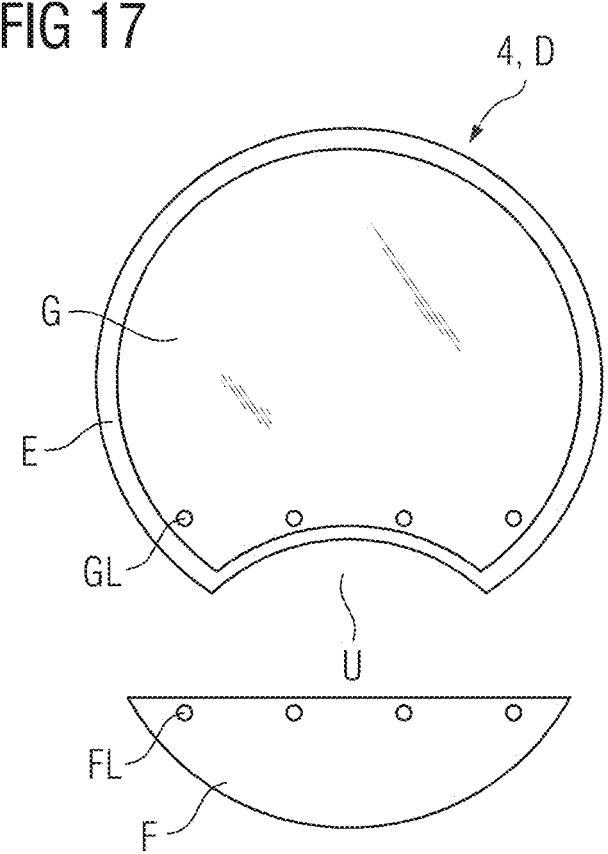
FIG. 17 shows an arrangement with a radiation protection body and a radiation curtain.

FIG. 17 shows an arrangement with a radiation protection body D and a radiation curtain F. The radiation curtain F can be detachably connected to the lead-glass panel G via the connecting elements FL and GL, via clipping on, for instance. The radiation curtain F covers the cut-out U, which is formed in the radiation protection body D.

Figure 18:
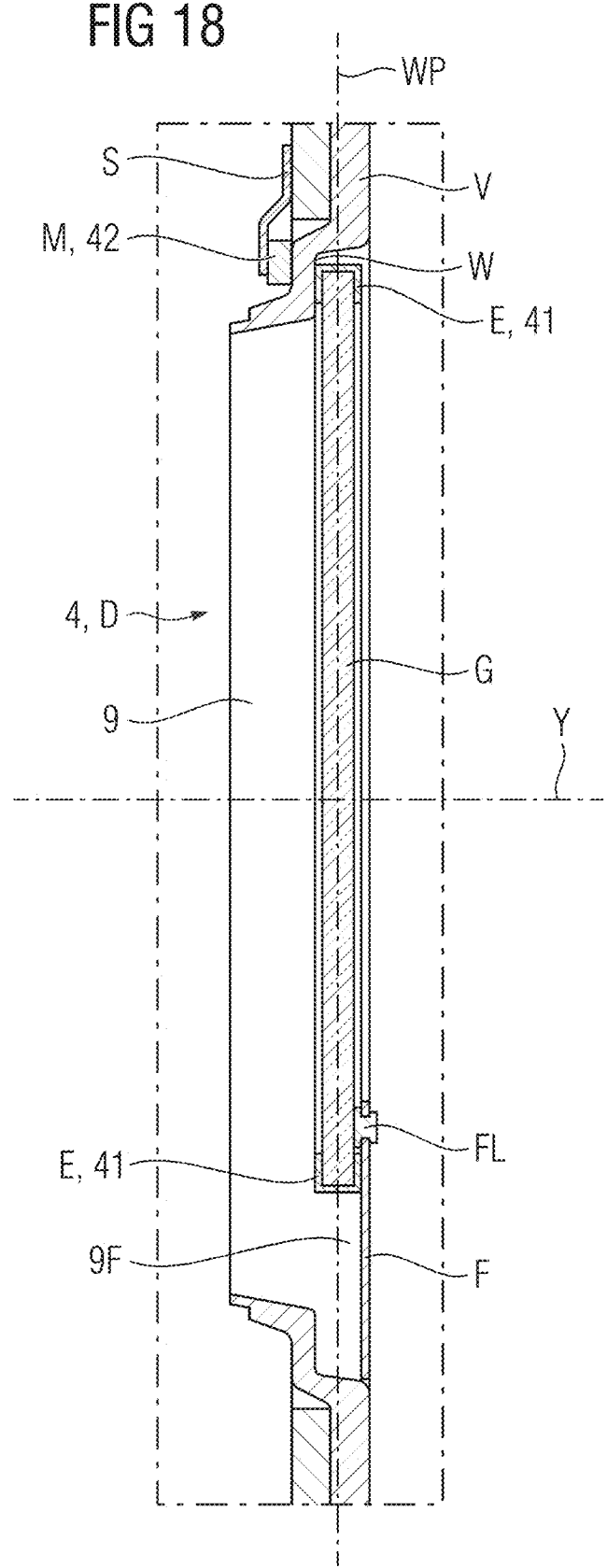
FIG. 18 shows a sectional view of a radiation protection apparatus with a radiation protection body, which is received in a recess in a form-fit manner.

FIG. 18 shows a sectional view of a radiation protection apparatus 4 with a radiation protection body D, which is received in the recess W in a form-fit manner.

Figure 19:
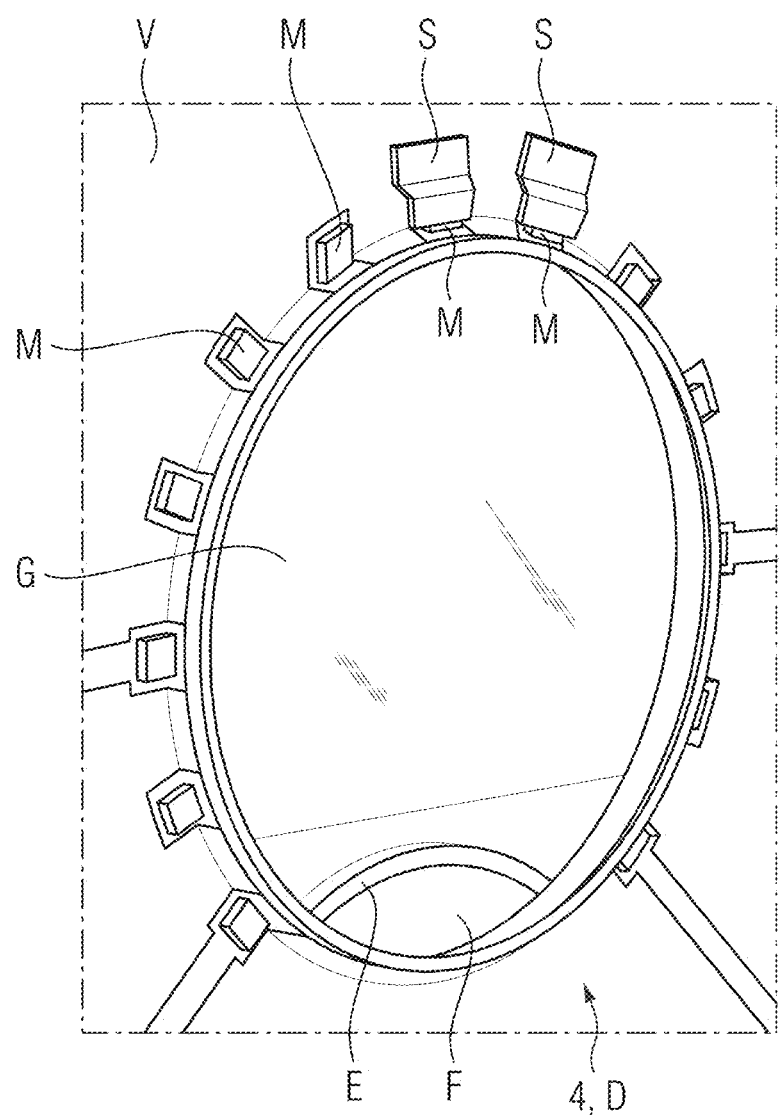
FIG. 19 shows a further view of a radiation protection apparatus with a radiation protection body, which is received in a recess in a form-fit manner.

FIG. 19 shows a further view of a radiation protection apparatus 4 with a radiation protection body D, which is received in the recess W in a form-fit manner.

The tunnel-shaped opening 9 extends along the system axis Y of the computed tomography device 1.

The radiation protection body D is plate-shaped and extends in a two-dimensional manner in a plane WP of the radiation protection body D, wherein the plane WP of the radiation protection body D is at right angles to the system axis Y of the computed tomography device 1, when the radiation protection body D is received in a form-fit manner in the recess W.

The recess W, in which the radiation protection body D can be received in a form-fit manner, is stepped and embodied to run annularly around the system axis Y of the computed tomography device 1. As a result, the radiation protection body D is secured in a form-fit manner against a relocation in the plane WP, if the radiation protection body D is received in the recess W in a form-fit manner.

The second connector 42 has a plurality of magnets M, which form an arrangement of magnets M which run annularly around the system axis Y of the computed tomography device 1. Each magnet M is received here in a form-fit manner in a recess provided herefor, in which it is held by a bracket S provided herefor. The holding frame E is ferromagnetic and is pulled by the magnet M and held in the recess W. The radiation protection body D does not project from the recess W. A secure and simple covering of the tunnel-shaped opening 9 is therefore possible.

Figure 20:
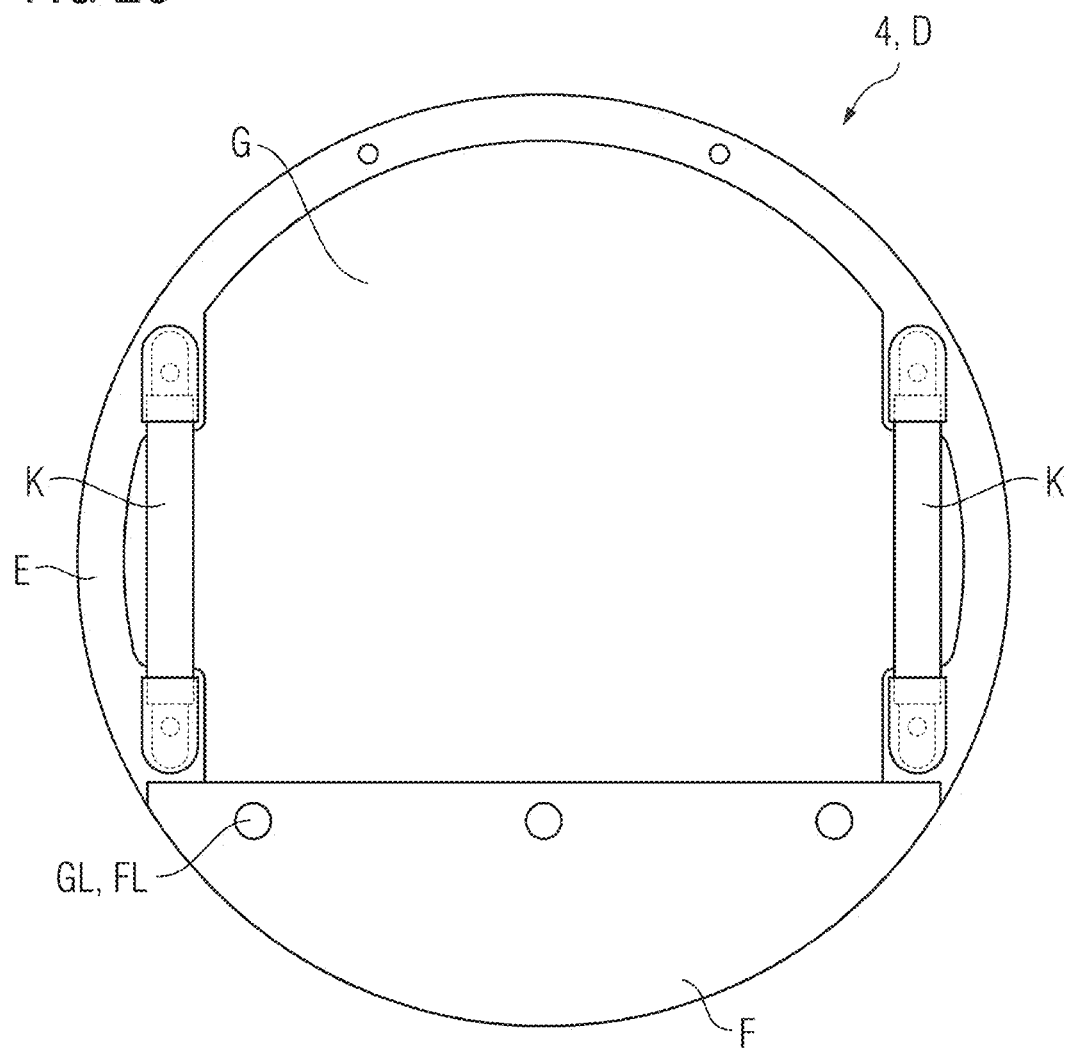
FIG. 20 shows a third example of a radiation protection apparatus with a radiation protection body and a radiation curtain.

FIG. 20 shows a third example of a radiation protection apparatus 4 with a radiation protection body D and a radiation curtain F, wherein each of the connecting parts K is embodied in each case in the form of a strap handle.

Figure 21:
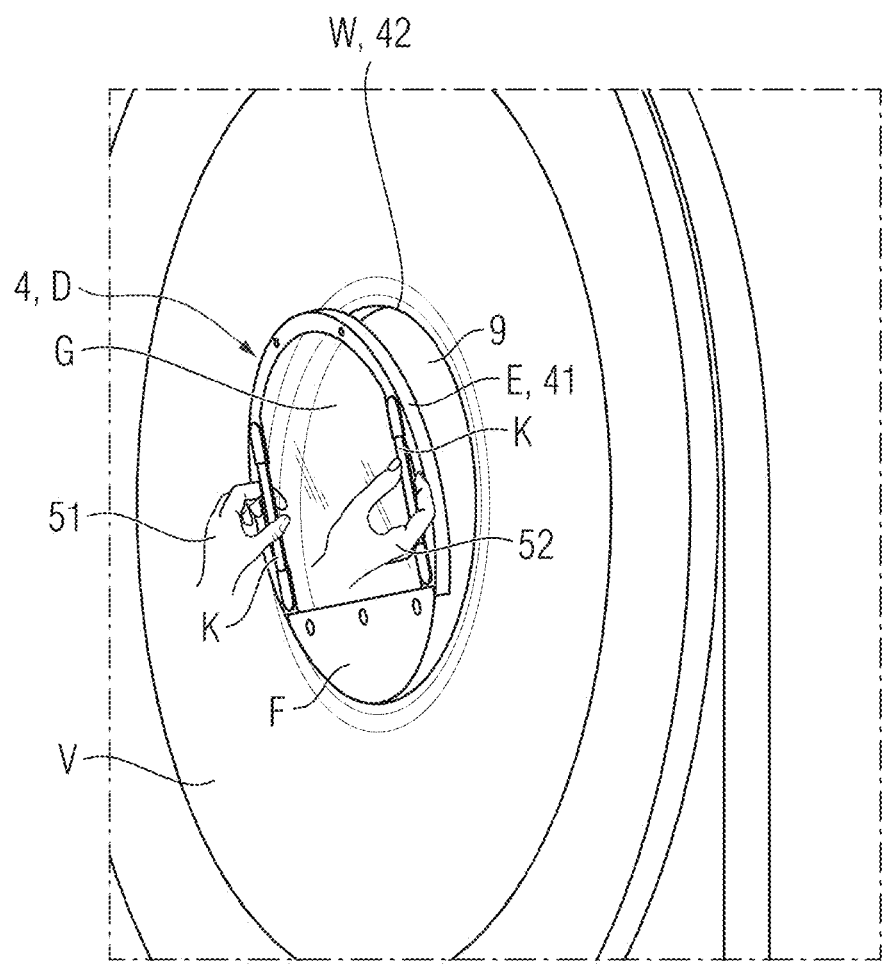
FIG. 21 shows a computed tomography device upon removal of a radiation protection apparatus, according to the third example, from the tunnel-shaped opening.

FIG. 21 shows a computed tomography device 1 upon removal of a radiation protection apparatus 4 according to the third example of the tunnel-shaped opening 9.

Figure 22:
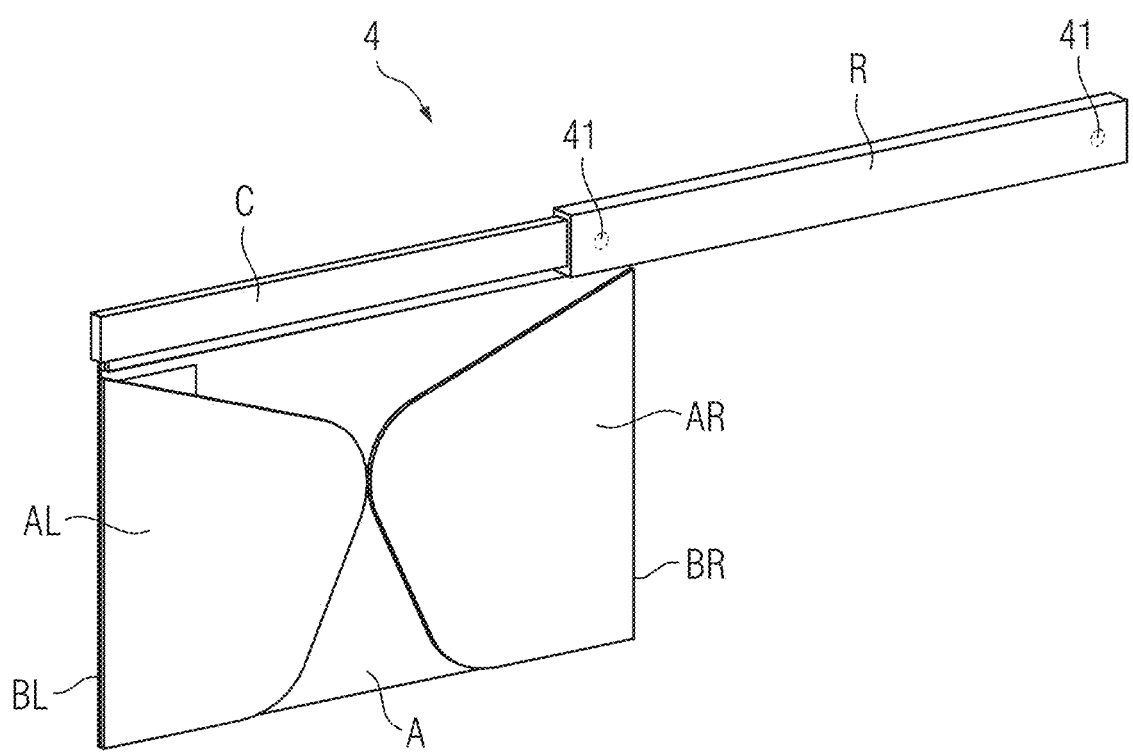
FIG. 22 shows a radiation protection apparatus with a sliding carriage on a rail according to a further example.

FIG. 22 shows a radiation protection apparatus 4 with a sliding carriage C on a rail R according to a further example. Each of the first connectors 41 has in each case a cut-out for receiving a fastening pin and a locking unit for detachable form-fit locking of the fastening pin in the cut-out.

The radiation curtain A has a first side wing AL, which is supported pivotably about the edge BL and a second side wing AR, which is supported pivotably about the edge BR. The side wing AL can be pivoted for instance about more than 180 degrees, in particular about more than 270 degrees, about the edge BL, starting from the position shown in FIG. 22, for instance in order to cover the left edge region 9L of the tunnel-shaped opening 9. The side wing AR can be pivoted for instance about more than 180 degrees, in particular about more than 270 degrees, about the edge BR, starting from the position shown in FIG. 22, for instance in order to cover the right edge region 9R of the tunnel-shaped opening 9.

Figure 23:
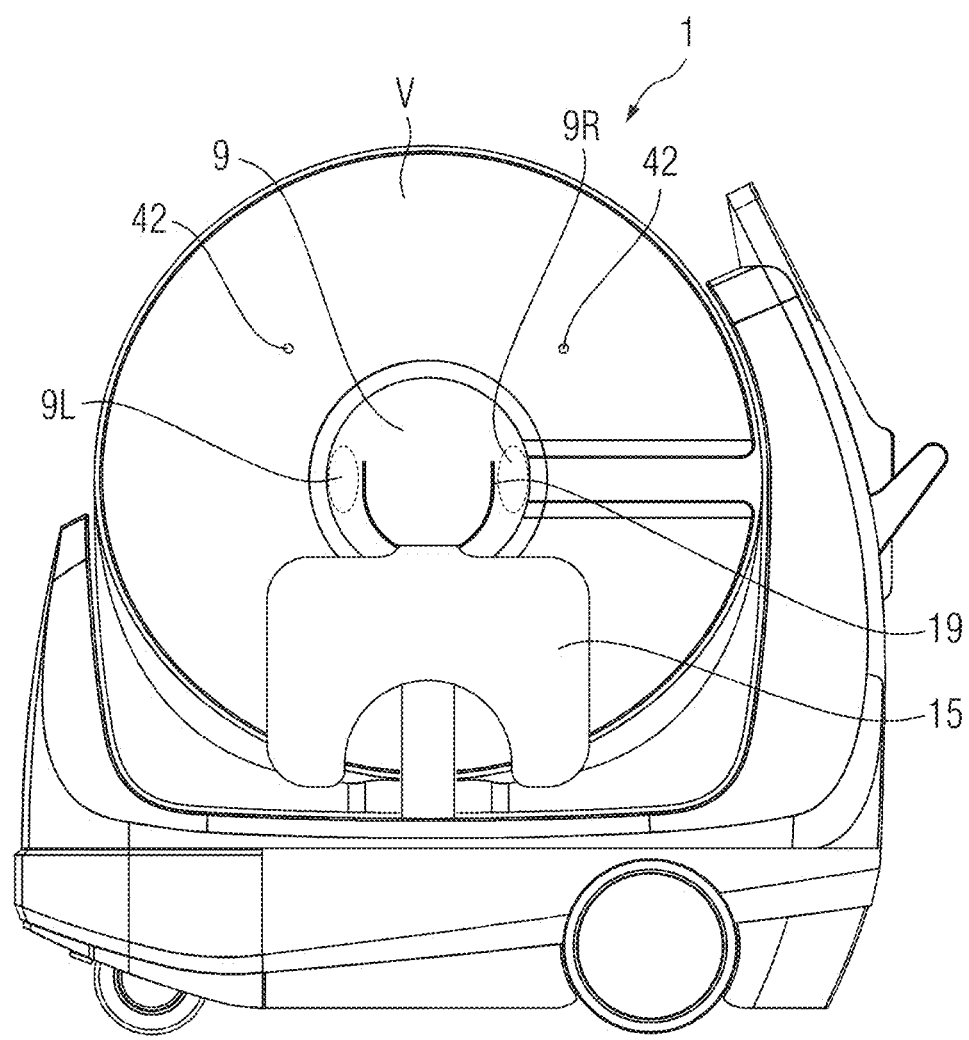
FIG. 23 shows a computed tomography device for an examination of a head of a patient according to a further example.

FIG. 23 shows a computed tomography device 1 for an examination of a head of a patient 13 according to a further example. Each of the second connectors 42 has in each case a fastening pin, which projects substantially parallel to the system axis Y in relation to the cladding V. A detachable connection, which counteracts a removal of the radiation protection apparatus 4 from the tunnel-shaped opening 9, can be formed via the first connectors 41 according to FIG. 22 and the second connectors 42 according to FIG. 23, by the fastening pins being received in the cut-outs provided therefor and being detachably locked therein in a form-fit manner.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A computed tomography device, comprising:
 a gantry including a tunnel-shaped opening, an examination object being introducible into the tunnel-shaped opening for an examination via the computed tomography device; and
 a radiation protection apparatus to cover the tunnel-shaped opening, the radiation protection apparatus including a first connector and the gantry including a second connector,
 wherein a detachable connection is formable via the first connector and the second connector, to counteract removal of the radiation protection apparatus from the tunnel-shaped opening.

2. The computed tomography device of claim 1,
 wherein the gantry includes a first gantry part and a second gantry part,
 wherein the first gantry part includes a rotatably supported rotor with a projection data acquisition system,
 wherein the second gantry part includes the second connector and at least one section of the tunnel-shaped opening, and
 wherein the first gantry part is supported movably in relation to the second gantry part, to enable a translational movement of the first gantry part in relation to the second gantry part to be carried out, while at a same time the second gantry part is at rest in relation to the examination object and the radiation protection apparatus is at rest in relation to the examination object and in relation to the at least one section of the tunnel-shaped opening upon the detachable connection being formed via the first connector and the second connector.

3. The computed tomography device of claim 2, wherein the first connector includes at least one ferromagnetic region and the second connector includes at least one magnet.

4. The computed tomography device of claim 2,
 wherein the radiation protection apparatus includes a radiation curtain and a rail for suspending the radiation curtain to be at least one of movable and mountable along the rail, and
 wherein the rail includes the first connector.

5. The computed tomography device of claim 4,
 wherein the gantry includes a cladding,
 wherein the cladding includes a recess in which the rail is receivable in a form-fit manner, and
 wherein the second connector is arranged in a region of the recess so that the detachable connection counteracts a removal of the rail from the recess upon the rail being received in the recess in a form-fit manner.

6. The computed tomography device of claim 2,
 wherein the radiation protection apparatus includes a radiation protection body,
 wherein the gantry includes a cladding,
 wherein the cladding includes a recess to receive the radiation protection body in a form-fit manner,
 wherein the radiation protection body includes the first connector, and
 wherein the second connector is arranged in a region of the recess to permit the detachable connection to counteract a removal of the radiation protection body from the recess upon the radiation protection body being received in the recess in a form-fit manner.

7. The computed tomography device of claim 1, wherein the first connector includes at least one ferromagnetic region and the second connector includes at least one magnet.

8. The computed tomography device of claim 7,
 wherein the radiation protection apparatus includes a radiation protection body,
 wherein the gantry includes a cladding,
 wherein the cladding includes a recess to receive the radiation protection body in a form-fit manner,
 wherein the radiation protection body includes the first connector, and
 wherein the second connector is arranged in a region of the recess to permit the detachable connection to counteract a removal of the radiation protection body from the recess upon the radiation protection body being received in the recess in a form-fit manner.

9. The computed tomography device of claim 1,
 wherein the radiation protection apparatus includes a radiation curtain and a rail for suspending the radiation curtain to be at least one of movable and mountable along the rail, and
 wherein the rail includes the first connector.

10. The computed tomography device of claim 9,
 wherein the gantry includes a cladding,
 wherein the cladding includes a recess in which the rail is receivable in a form-fit manner, and
 wherein the second connector is arranged in a region of the recess so that the detachable connection counteracts a removal of the rail from the recess upon the rail being received in the recess in a form-fit manner.

11. The computed tomography device of claim 9, wherein the radiation curtain is detachably connected to the rail.

12. The computed tomography device of claim 9, wherein the radiation curtain includes a lead-glass window.

13. The computed tomography device of claim 12, wherein the radiation curtain includes a strip-shaped region made from a flexible radiation protection material, arranged between the lead-glass window and the sliding carriage.

14. The computed tomography device of claim 1,
 wherein the radiation protection apparatus includes a radiation curtain and a sliding carriage, the radiation curtain being connected to the sliding carriage and mounted along the sliding carriage,
 wherein the gantry includes a rail to support the sliding carriage, the gantry being movable along the rail,
 wherein the sliding carriage includes the first connector, and
 wherein the rail includes the second connector.

15. The computed tomography device of claim 1,
 wherein the radiation protection apparatus includes a radiation protection body,
 wherein the gantry includes a cladding,
 wherein the cladding includes a recess to receive the radiation protection body in a form-fit manner,
 wherein the radiation protection body includes the first connector, and
 wherein the second connector is arranged in a region of the recess to permit the detachable connection to counteract a removal of the radiation protection body from the recess upon the radiation protection body being received in the recess in a form-fit manner.

16. The computed tomography device of claim 15,
wherein the tunnel-shaped opening extends along a system axis of the computed tomography device,
wherein the radiation protection body extends in a two-dimensional manner in a plane of the radiation protection body, and
wherein the plane of the radiation protection body is at right angles to the system axis of the computed tomography device upon the radiation protection body being received in the recess in a form-fit manner.

17. The computed tomography device of claim 15,
wherein the radiation protection body includes a lead-glass panel and a holding frame for the lead-glass panel,
wherein the lead-glass panel is fixed in the holding frame, and
wherein the holding frame is receivable in the recess in a form-fit manner to form the first connector.

18. The computed tomography device of claim 15,
wherein the radiation protection body is embodied so that a subregion of the tunnel-shaped opening is not covered by the radiation protection body upon the radiation protection body being received in the recess in a form-fit manner,
wherein the radiation protection apparatus includes a radiation curtain to cover the subregion of the tunnel-shaped opening, and
wherein the radiation curtain is connected to the radiation protection body so that the radiation curtain covers the subregion of the tunnel-shaped opening upon the radiation protection body being received in the recess in form-fit manner.

19. The computed tomography device of claim 18, wherein the subregion of the tunnel-shaped opening is configured to permit a hand to be introducible at least partially into the subregion of the tunnel-shaped opening so that an edge region of the radiation protection body adjoining the subregion (9F) of the tunnel-shaped opening is graspable with the hand subsequent to the radiation protection body being received in the recess in a form-fit manner.

20. The computed tomography device of claim 15, wherein the radiation protection apparatus includes a connecting part, connected to the radiation protection body, embodied to receive a tensile force to remove the radiation protection body from the recess, subsequent to the radiation protection body being received in the recess in a form-fit manner.

21. A method for an examination of an examination object via a computed tomography device, the computed tomography device including a gantry including a tunnel-shaped opening and a radiation protection apparatus to cover the tunnel-shaped opening, the radiation protection apparatus including a first connector and the gantry including a second connector, the gantry including a first gantry part and a second gantry part, the first gantry part including a rotatably supported rotor with a projection data acquisition system and the second gantry part including the second connector and at least one section of the tunnel-shaped opening, the first gantry part being supported to be movable in relation to the second gantry part, the method comprising:
introducing the examination object into the tunnel-shaped opening of the gantry, for the examination via the computed tomography device, wherein a detachable connection is formed via the first connector and the second connector to counteracts a removal of the radiation protection apparatus from the tunnel-shaped opening; and
carrying out a translational movement of the first gantry part in relation to the second gantry part, while simultaneously the second gantry part remains at rest in relation to the examination object and while the radiation protection apparatus remains at rest in relation to the examination object and in relation to the at least one section of the tunnel-shaped opening.

22. The method of claim 21, wherein the examination object is a head of a patient, and wherein the carrying out of the translational movement of the first gantry part in relation to the second gantry part, occurs while, at a same time, the radiation protection apparatus touches the patient.

23. The method of claim 22, wherein the carrying out of the translational movement occurs along a system axis of the computed tomography device, the system axis of the computed tomography device being an axis of rotation of the rotor of the computed tomography device.

24. The method of claim 21, wherein the carrying out of the translational movement occurs along a system axis of the computed tomography device, the system axis of the computed tomography device being an axis of rotation of the rotor of the computed tomography device.

* * * * *